United States Patent [19]

Buckles

[11] 4,321,057
[45] Mar. 23, 1982

[54] METHOD FOR QUANTITATIVE ANALYSIS USING OPTICAL FIBERS

[76] Inventor: Richard G. Buckles, 53 Gellerstrasse, 4052 Basel, Switzerland

[21] Appl. No.: 76,984

[22] Filed: Sep. 20, 1979

[51] Int. Cl.³ .......................................... G01N 21/64
[52] U.S. Cl. ............................. 23/230 B; 23/230 R; 356/445; 422/58; 422/60; 422/68; 435/7
[58] Field of Search ...................... 422/73, 68, 55–60; 23/230 B, 230 R; 356/445, 448, 435; 435/7

[56] References Cited

U.S. PATENT DOCUMENTS

| | | |
|---|---|---|
| 3,068,739 | 12/1962 | Hicks et al. . |
| 3,404,962 | 10/1968 | Medlar et al. .......................... 422/86 |
| 3,526,480 | 9/1970 | Findl et al. . |
| 3,817,706 | 6/1974 | Smith . |
| 3,866,599 | 2/1975 | Johnson . |
| 3,905,767 | 9/1975 | Morris et al. . |
| 3,907,503 | 9/1975 | Betts et al. . |
| 3,932,133 | 1/1976 | Ishikawa . |
| 3,992,158 | 11/1976 | Przybylourcz et al. . |
| 3,998,591 | 12/1976 | Eckfeldt ........................... 422/86 X |
| 4,042,335 | 8/1977 | Clément . |
| 4,050,895 | 9/1977 | Hardy et al. .................. 23/230 B X |
| 4,050,898 | 9/1977 | Goffe et al. . |
| 4,066,403 | 1/1978 | Bruschi . |
| 4,080,075 | 3/1978 | Berg ................................ 356/435 X |
| 4,099,882 | 7/1978 | Andrein et al. ..................... 356/411 |
| 4,200,110 | 4/1980 | Peterson et al. ............... 23/230 B X |

FOREIGN PATENT DOCUMENTS 2744678 4/1979 Fed. Rep. of Germany ...... 356/435

OTHER PUBLICATIONS

*Clinical Lab Products*; Oct. 1978, vol. 7, No. 10.
"Imagine Clinical Chemistry Right in the Palm of Your Hand;" Eastman Kodak Co.; 1978.
"Spreading Layer Function and Properties;"T. W. Eder et al; presented–Int. Cong. of Clinical Chem; 3/78 (Mexico City).
"A New Technology for the Clinical Laboratory;" E. P. Przybylowicz; presented–Amer. Assoc. for Clinical Chemistry; 7/78 (San Francisco, Ca.).
"Ektachem Analyzer Instrumentation Functions;" R. L. Sanderson et al; presented–Amer. Assoc. for Clinical Chem. (7/78–San Francisco, Ca.).
"Instrumentation Requirements and General Concepts;" J. E. Pinney et al., presented–Int. Congr. of Clinical Chem.; 3/78 (Mexico City).
"New Integral Analytical Element for Serum Assay;" K. C. Kennard; presented–Int. Congr. of Clinical Chem; 3/78 (Mexico City).

*Primary Examiner*—Barry Richman
*Attorney, Agent, or Firm*—Kenway & Jenney

[57] ABSTRACT

A method and apparatus for chemical and biochemical analyses which employ an energy-transmissive core and may employ one or more sheaths which selectively absorb, react with, and/or filter an analyte or a product of an analyte. The core is transmissive to a chosen energy carrier and it has an inlet end and an outlet end. Between these ends it has an extended length. The passage of energy through the core is modified by reason of events which occur in one or more of the sheaths or in the case where no sheath is employed, by reason of events which occur in an ambient fluid. The resulting modification of the transmitted energy is a measure of such events which in turn are a measure of the analyte. The energy may be any of several types of energy which can be transmitted through the core from end to end and which is susceptible to modification by reactions in the sheath or sheaths or ambient fluid. The energy may be electromagnetic, electrical or sonic. In the method aspect of the invention a permeable core may be used which is bare, i.e. without a sheath, and exposed directly to an environment, e.g. the air or an industrial fluid.

22 Claims, 23 Drawing Figures

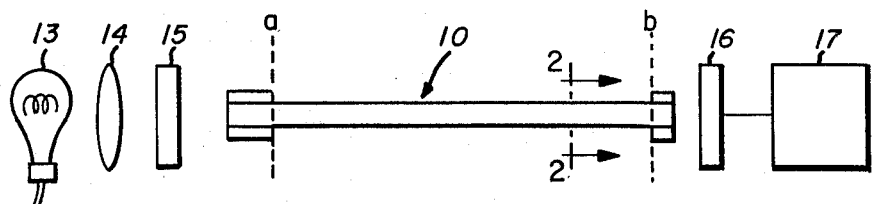
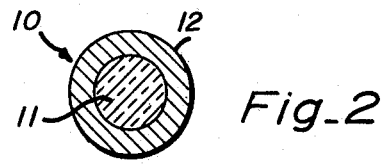
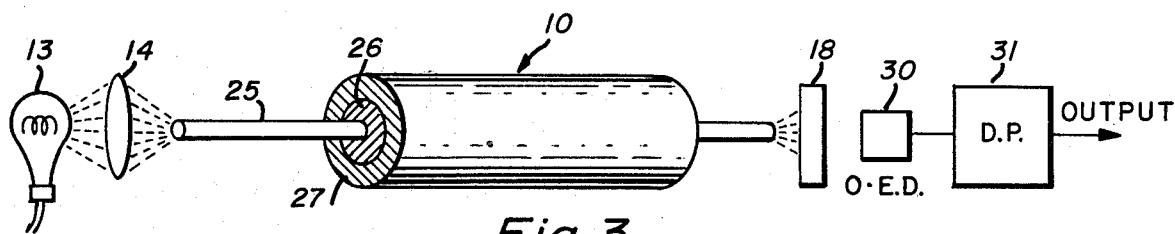
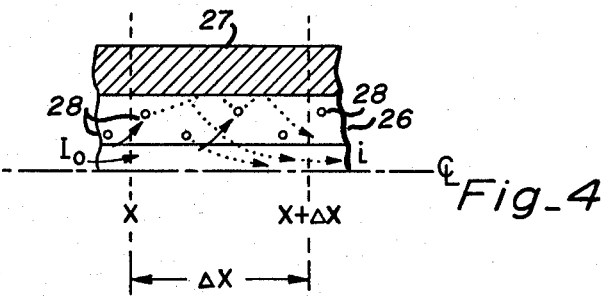
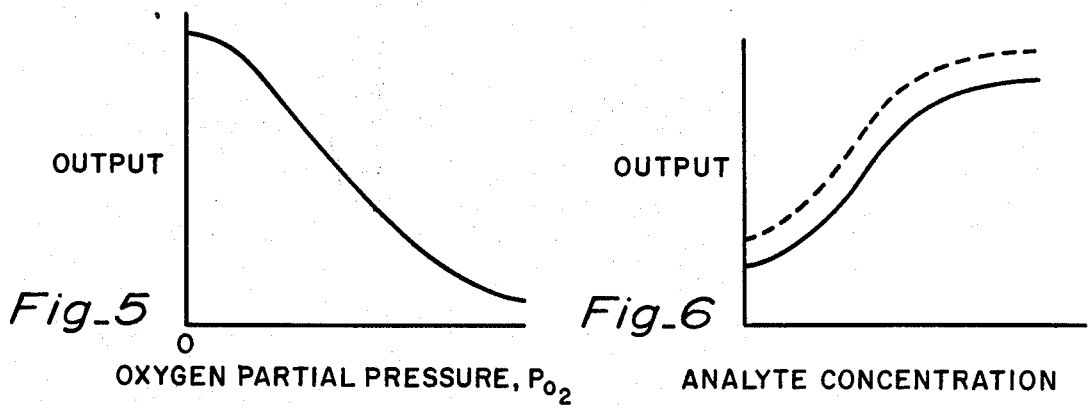
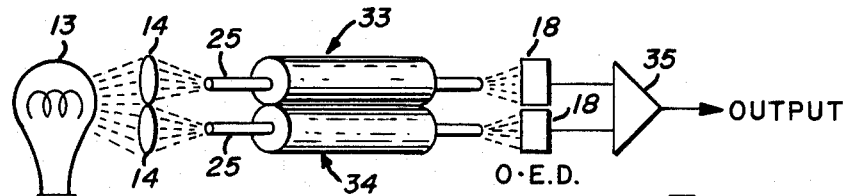

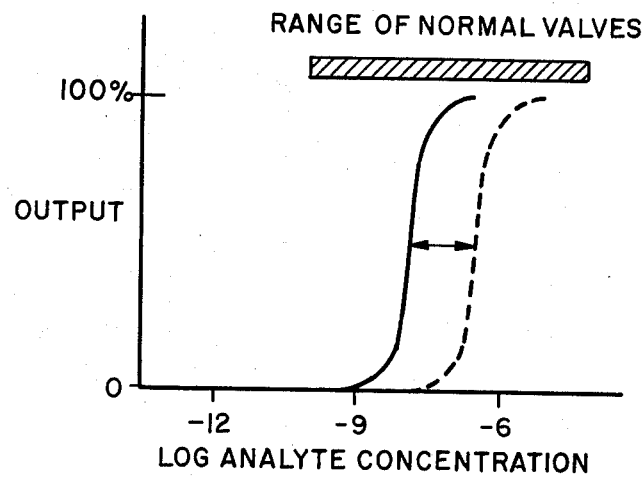
Fig_8
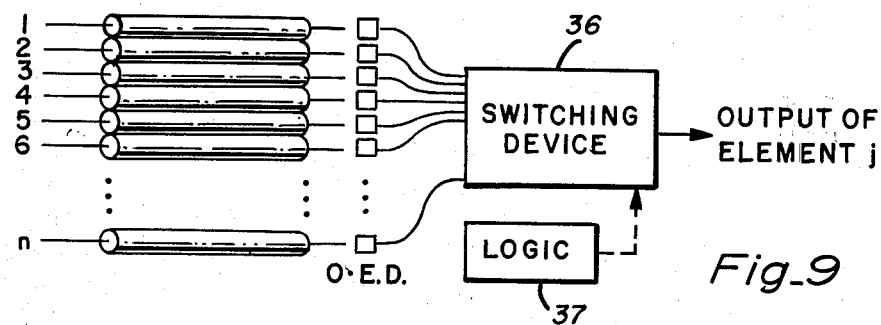
Fig_9
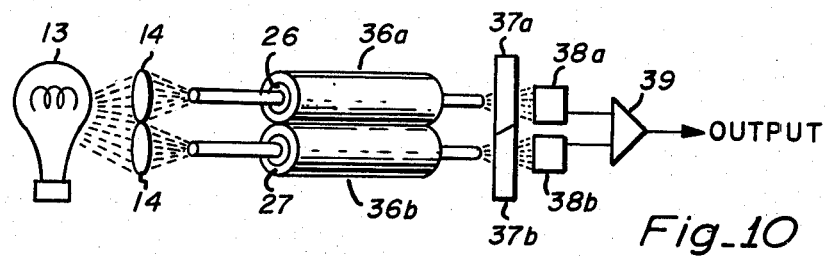
Fig_10
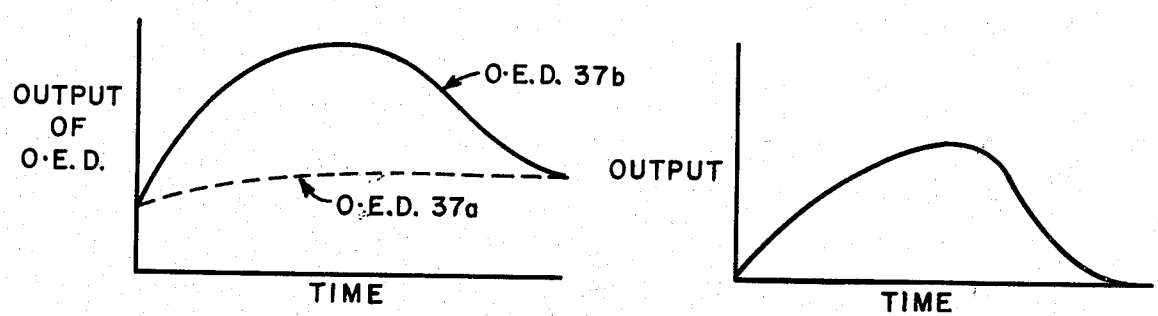
Fig_11
Fig_12

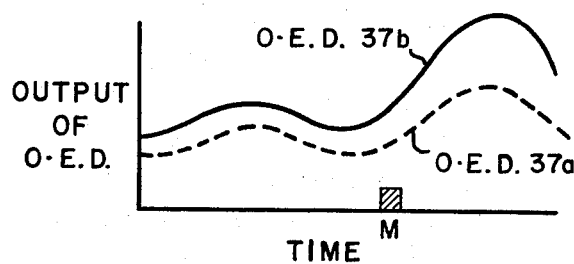
Fig_13
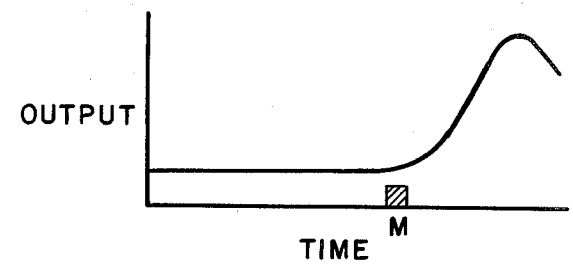
Fig_14
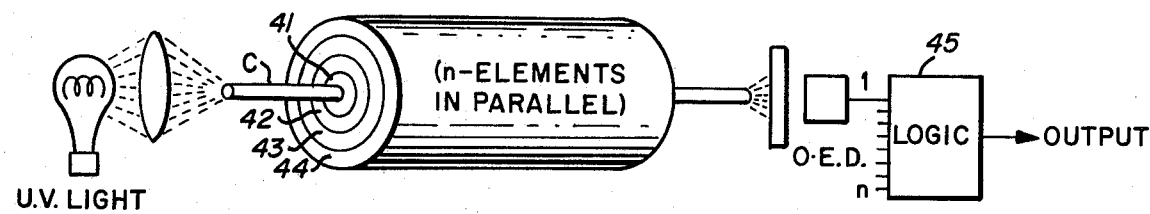
Fig_15
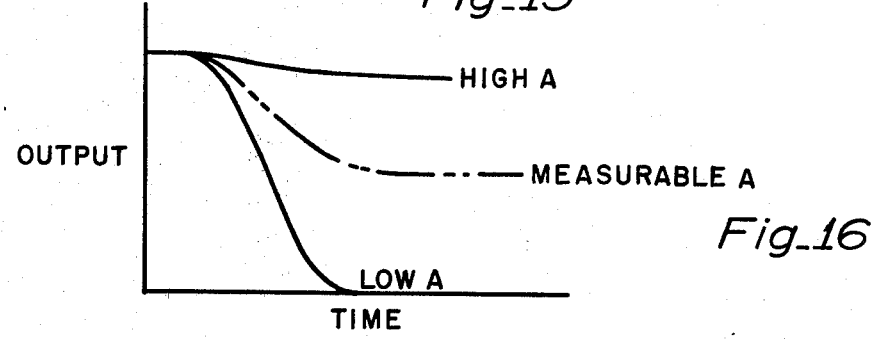
Fig_16
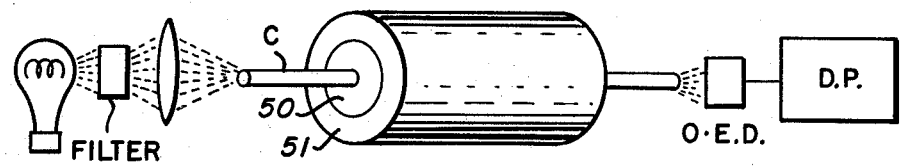
Fig_17
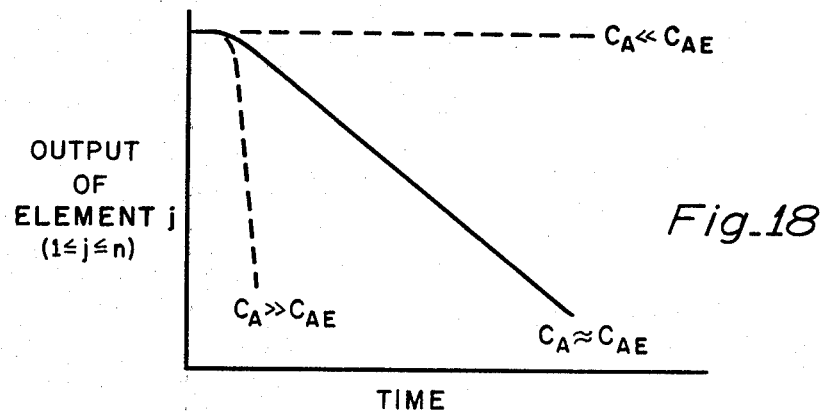
Fig_18

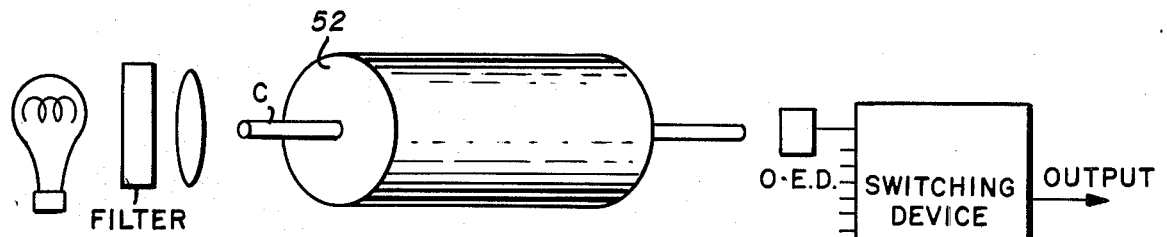
Fig_19
Fig_22
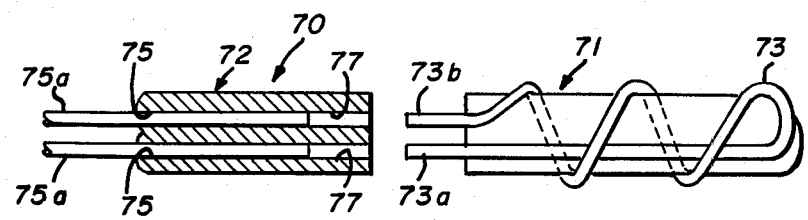
Fig_23
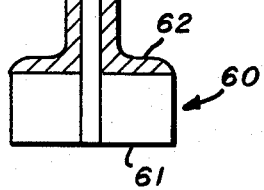
Fig_20
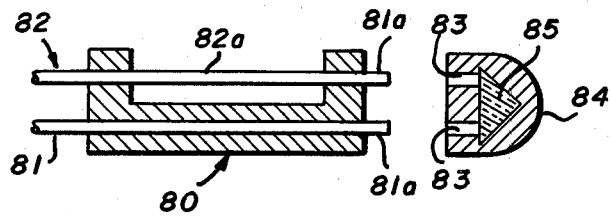
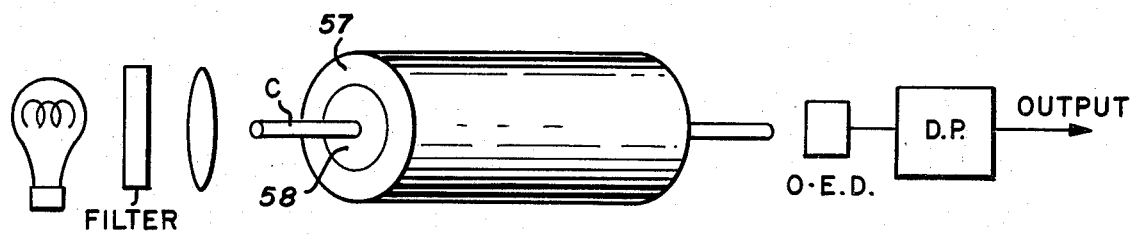
Fig_21

METHOD FOR QUANTITATIVE ANALYSIS USING OPTICAL FIBERS

Many analytical techniques have been developed for chemical or biochemical purposes. Procedures that use a discrete fluid sample for analysis of a single analyte are traditionally characterized as wet chemical techniques or dry chemical techniques. In recent years both types of techniques have been automated in order to reduce costs and simplify procedures. Wet chemical methods, typified by the Technicon auto analyzers, utilize batches of reagent solutions, pumps and fluid controls, coupled with conventional sensors, (such as densitometric, fluorescent, colormetric (i.e. radiometric), polarographic, conductimetric, or ultrasonic). These techniques are characterized by large equipment, generally expensive, and generally requiring a skilled operator.

Dry chemical techniques utilize reagents stored under dry conditions within a single or multi-layer flat element such that a test liquid will result in a reaction that can be radiometrically detected (see U.S. Pat. No. 3,092,465). These techniques are simple to use, but have traditionally yielded only qualitative results. There are several reasons for this that have been well explained in recent U.S. patents assigned to Eastman Kodak (see U.S. Pat. Nos. 3,992,158, 4,042,335 and 4,066,403). The major reasons are: non-uniform spreading of the fluid over the flat surface; non-uniform penetration of the fluid or analyte into the region where the reagent is stored; and non-uniform effects at the edges of the spread liquid. The well-known "dip stick" products had to utilize chemical reactions that proceeded to completion because their transient response characteristics were temperature dependent and they were used in a non-thermostatted environment. A new system of dry chemistry has been recently introduced by Eastman Kodak claiming to overcome many of the traditional weaknesses of dry chemical methods.

The Kodak technique utilizes flat, multilayered sheets arranged in sequence such that the top layer receives the liquid sample and it passes downward undergoing separations and reactions in a pre-arranged sequence. The sheet is designed to accept a small volume of liquid and distribute it uniformly over a reproducible area; the area is less than the total area of the multi-laminar sheet. Each layer of the sheet is essentially homogeneous in a direction parallel to the surface; thus, once spread radially (a rapid process) the components of the liquid can move downward at rates that are essentially the same in any plane that is parallel to the surface. In this way uniform reactions, filtrations, etc. can occur.

The analyte is detected in such multilayered sheets by radiometric methods, carried out in a thermostatted environment. This permits one to use kinetic measurements as well as static ones in order to detect analyte concentrations in the liquid sample.

Radiation is caused to enter this assembly in a path which is transverse to the several layers. The radiation is modified by the analyte or by a component or product of the analyte. For example, the exciting radiation may be partially absorbed by the analyte or by a component or product of the analyte. The modified radiation may be reflected back transversely through the laminar assembly or it may pass through the entire assembly. In either case (reflection or transmission) the path of the exciting radiation is very short and is determined by the thickness of the layer in which the exciting radiation encounters the substance which is excited. Since this dimension must be very small to permit rapid measurement, e.g., 10 $\mu$m to 100 $\mu$m the degree of modification of the exciting radiation is quite small. This limits the applicability of this technique to analyses wherein the analyte (or a component or product of the analyte) interacts very strongly with the exciting radiation or it requires the use of very sensitive detecting apparatus. It has been shown to be a useful method for measuring analytes in blood that exist at relatively high concentrations, e.g., glucose, BUN, cholesterol, albumin.

Other analytical methods have been developed that utilize rapidly reversible chemical reactions in order to continuously monitor analyte concentrations in biological fluids, or industrial effluent streams, or ponds, lakes and streams. For example, several methods have been proposed to measure the oxygen level in blood of critically ill patents.

It is an object of the present invention to provide improvements in analytical procedures and apparatus.

It is a further and more particular object of the present invention to provide an analytical technique (both method and apparatus) by which a laminar assembly of the general type described above can be employed without the limitations inherent heretofore.

The above and other objects of the invention will be apparent from the description below and the appended claims.

In accordance with the present invention a core is provided which is transmissive to the chosen energy, which may be electromagnetic (e.g. ultraviolet or visible light), electronic or sonic energy. This core is provided with one or more permeable or semi-permeable sheaths (i.e. permeable to a fluid sample containing the analyte, or permeable to so much of the test fluid as is desired but acting to filter out unwanted components). This part of the apparatus may be referred to as the "sheath structure" signifying that it may consist of one or more permeable or semi-permeable sheaths. As will appear more fully from the description below, there are several functions that may be performed by the sheath structure any one or more of which may be performed by one or more of the individual sheaths.

The core, as stated, is transmissive to the chosen energy and causes that energy to pass in a direction generally parallel to the surface to which the test fluid is applied. The core has an "active length" which, as will appear more fully hereinafter, is that portion of its length, usually but not necessarily less than the entire length of the core, wherein the energy passing through the core is subjected to the influence of the test fluid and is modified thereby. The magnitude of this active length is large, and as will appear more fully hereinafter it is very large compared to the thickness of the sheath structure and/or the core. By this arrangement the energy passing through the core along its active length is subjected to a cumulative, although not necessarily uniformly cumulative, modification by reason of the presence of analyte in the test fluid.

As will also appear more fully hereinafter, the core, if permeable to an analyte in a liquid or gaseous test fluid, or to a product of such analyte, may be bare, i.e. devoid of a sheath structure and may therefore be in direct contact with the test fluid.

The physical shape and configuration of the device or apparatus of the invention may vary considerably. In a preferred embodiment, the device is cylindrical and consists of a central core or fiber which is transparent to the exciting radiation and is surrounded by a sheath structure consisting of one or more concentric layers of absorptive material. Alternatively the shape in cross section may be polygonal with one or more absorptive layers surrounding the transmissive layer.

In any such configuration, the path of the carrier energy is generally parallel to, rather than transverse to the overlying layer or layers. Many of the figures in the drawings will serve to illustrate various embodiments of the invention. For the most part the carrier energy will be described as electromagnetic radiation.

BRIEF DESCRIPTION OF THE DRAWINGS

FIGS. 1 to 4 depict an embodiment of the invention wherein a single inner core-outer sheath configuration is used.

FIGS. 5 and 6 show typical curves of the relationship of the output of electrical energy produced from the emitted light energy and the analyte concentrations.

FIG. 7 depicts an embodiment of the invention wherein two parallel fiber assay devices (FAD) are used.

FIG. 8 depicts a range limitation of highly sensitive assay systems.

FIG. 9 depicts a multiple fiber assay device (MFAD) configuration of the invention.

FIGS. 10 to 12 depict a dual FAD designed for glucose determinations.

FIGS. 13 and 14 depict a continuous monitoring case for the use of a dual FAD.

FIGS. 15 and 16 depict a multi-sheathed single FAD of a multiple FAD system.

FIGS. 17 and 18 depict an embodiment of the invention designed for high sensitivity immunoassays.

FIG. 19 depicts a single sheath-inner core embodiment wherein the sheath has a lower refractive index than the core.

FIG. 20 depicts a wicking means for uniformly saturating a FAD.

FIG. 21 depicts a device of the invention designed for enzyme determinations in fluid samples.

FIGS. 22 and 23 depict embodiments of the invention wherein the fiber is incorporated into a catheter structure.

In FIG. 1 there is shown one form of the apparatus of the present invention which is generally designated by the reference numeral 10 and which, as shown in the cross sectional view of FIG. 2, consists of an inner core of fiber 11 and an outer sheath 12. The core or fiber 11 is transparent to the exciting radiation but, instead of being a conventional optical fiber such as quartz fiber, it is selected so that it is not only optically transmissive but is also permeable to components of an aqueous solution. The outer sheath 12 is of absorptive, semipermeable material.

To the outer sheath 12 is applied, for example by immersion or dipping, a fluid containing the analyte under consideration, for example blood where it is desired to measure one of its low molecular weight components. If it is desired to prevent penetration by large molecules and formed elements such as erythrocytes, platelets, or white cells, the material of which the sheath 12 is constructed may be suitably selected so as to filter out such large molecules and elements. Alternatively an outer layer (not shown) may be provided which is permeable to water, and small molecules but which is impermeable to large molecules and formed elements of the blood. Thus, it is understood that one function of layer 12 is to act as an impermeable barrier to those unwanted components of the test fluid.

When the device 10 is immersed in the test fluid, for example, in blood, the fluid will penetrate to the core of fiber 11. Its presence may be detected by illuminating the core with (e.g.) light of a wavelength that is selectively absorbed by the analyte. Thus the diminution of light that emerges from the exit end of the fiber is proportional to the concentration of the analyte in the sample fluid.

In FIG. 1 there is shown diagramatically a system for carrying out such a determination of analyte in an aqueous solvent, including a source of radiation 13, a focussing lens 14 and a suitable filter 15 to transmit light of the proper wavelength. At the exit end of the device is a light detector 16 and an electrical signal processor 17. The electrical signal processor amplifies the signal from the light detector and may be made from any of several well known and commercially available devices, and may include readout means of visual type and a recorder for a printed readout.

It is to be understood that the instruments of FIG. 1 that are used to introduce energy into the analytical apparatus and to measure that which leaves the system can be configured in any of a number of ways depending on the use of the device. The simplicity of use and intrinsically rapid response of the invention suggests that one use will be to make bedside measurements. In such a case a portable unit with rechargeable batteries would be preferred. It is to be further understood that modern electronic data processing methods are so compact that one may further simplify the use of the analytical apparatus by utilizing electronic corrections and calibrations which permit the use of assay methods that are non-linear in their response to the analyte concentration. In fact, it is possible to assemble several analytical elements in a parallel arrangement in a single instrument.

The letters "a" and "b" and the lead lines therefrom in FIG. 1 signify the "active length" of energy transmissive device 10. This active length is that portion of the device which is exposed to analyte, or to a product of an analyte, and along which the flow of energy is cumulatively modified by the analyte or a product of the analyte. The path from "a" to "b" (which may be continuous or segmented, is long compared to the thickness of the element 10.

In the apparatus of FIG. 1 the core 11 may be bare, i.e. devoid of a sheath. Thus where, for example, the atmosphere or water, an industrial fluid or a biological fluid contains the analyte of interest, e.g. a contaminant such as sulfur dioxide or a nitrogen oxide in stack gas or a phenolic contaminant, the material of the core 11 may be selected so that it absorbs such contaminant which modifies the flow of energy through the core, e.g. by absorption of a selected wavelength of light.

Referring now to FIG. 3, a system similar to that of FIG. 1 is shown where the fiber assay device (FAD) 10 shown on a larger and exaggerated scale and with the interior exposed to show the several components including a core 25 (hereinafter designated by the letter "C") which is transmissive to ultraviolet radiation and is impermeable to fluids; and a sheath 26 of gas permeable material containing an oxygen quenchable fluorescent dye substance. The index of refraction $n_s$ of sheath 26 is greater than the index of refraction $n_c$ of the core. The outer sheath 27 is oxygen permeable and is reflective. It may be impermeable to large molecules and to formed elements such as platelets and red cells in blood.

Referring to FIG. 4, which is a fragmentary cross section through the FAD, molecules of fluorescent dye are indicated at 28. Ultraviolet light passes through the core and some of it is refracted into the sheath 26 where it reacts with fluorescent molecules which emit radiation in the visible spectrum; such emission is isotropic. That visible radiation which impinges upon the interface between the sheaths 26 and 27 is reflected into the core along with radiation which enters the core directly. Assuming, as will be the case in practice, uniformity of distribution of fluorescent molecules in the sheath 26, during passage through each increment of length of the core $\Delta X$, (X being the distance along the active length of the core) the radiation passing through the core will pick up an increment $\Delta i$ of emitted light. $\Delta i$ will not, of course, be constant inasmuch as the UV radiation is somewhat attenuated as it passes through the core 25. Nevertheless a cumulative effect will occur and the intensity of emitted visible light $$\sum_{0}^{x} \Delta i$$

will be much greater than the value of $\Delta i$ emerging from a small segment of the path.

When a fluid, for example blood, industrial water or river water containing oxygen (which is the analyte to be determined) is applied to the outer sheath 27, it will penetrate to the sheath 26. The dissolved oxygen in the fluid will quench fluorescence, therefore, it will diminish the intensity of fluorescent light emitted at the output end of the core. The emitted radiation passes through the ultraviolet filter 18, then through an opto-electrical detector (O-E.D.) 30 which acts as a transducer to convert the emitted light energy into electrical energy. The emitted electrical energy is processed in a unit 31 resulting in a digital or analog output. A suitable processor consists of amplifiers, limiters, meters, and elements for electrical logic, as are well known to those in the instrumentation business. A molecule well known for its tendency to exhibit $O_2$ quenching of fluorescence is fluoranthrene.

FIG. 5 shows a curve typical of such an output. Advantageous features of this system include its low temperature sensitivity, any rapid response time.

Referring now to FIG. 6, a plot of analyte concentration against output of a similar system is shown.

The solid curve represents a mean calibration curve in the absence of other molecules. The dotted curve is the calibration curve in the presence of a molecule that may also occur in the fluid. Thus, the calibration curve shifts up or down the vertical axis as a function of the unknown concentration of contaminant, $C_c$. If $C_A$ is the concentration of the analyte, we may represent this phenomeon of interference by the expression:

OUTPUT$\alpha(C_A+C_c)$ where $\alpha$ represents a proportionality. In order to obtain an output that is independent of $C_c$ one would traditionally have to remove C by some chemical process, or measure it by an independent method. However, the present invention lends itself to a double fiber assay (DFA) system which dispenses with the need for calibration, such being shown in FIG. 7. As shown in FIG. 7 there are two FAD units one of which 33 measures the output shown in FIG. 5; the other being a unit 34 which is designed so as to measure the concentration of contaminant C. The output of the two fibers can be detected with equal sensitivity because the fibers are illuminated from a single light source. The two signals can be electronically subtracted as can be done in commercially available analogue or digital devices indicated generally at 35. Therefore without the need for calibration the output is a measure of the concentration of analyte.

Yet another limitation of many highly sensitive assay systems (e.g. radioimmune assay) is summarized in FIG. 8. The analyte is detected by reaction with a reagent. The high specificity of the reaction leads to a steep dose response curve; i.e. for a given reagent concentration the output changes over its full range when traversing a narrow range of analyte concentration. When the range of anticipated analyte concentration is wide, as denoted by the shaded area in FIG. 7, one must perform several determinations, each with a different reactant concentration in order to determine the analyte concentration.

Referring now to FIG. 9, a multiple fiber assay device (MFAD) is shown consisting of n such FAD devices, each of which embodies within one of its sheaths a reagent. The reagent concentrations vary from one device to the other. It will be apparent that when these fibers are wet by a fluid that there is one reagent concentration resulting in an output which is a reflection of the analyte concentration. The other fibers either over- or under-react with the analyte yielding unmeasurable outputs. Assume that $FAD_j$ (j being an integer from one to n) is optimum. The separate outputs of the FADs are converted by O-E.D.s to electrical outputs which are separately transmitted to a switching device 36 controlled by a microprocessor 37 to select the output of $FAD_j$ and reject the others.

Referring now to FIG. 10, a dual FAD system is shown intended for the determination of the glucose concentration of a body fluid, for example blood. As in FIG. 3, sheath 26 of each device contains an oxygen guenchable dye and sheath 27 is an oxygen permeable sheath which reflects light back into the core. The sheath 27 also functions to prevent penetration of fluorescent molecules from the sample. Alternatively, an outermost sheath (not shown) may be employed for that purpose. One such device 36a is the control device that measures oxygen (the contaminant); and the other 36b is modified by having in the sheath 27 a quantity of glucose oxidase. Both devices are wetted with a sample simultaneously. Oxygen in both samples penetrates through sheath 27 to sheath 26 and quenches fluorescence. However, glucose oxidase in sheath 26 of device 36b causes reaction of a portion of the oxygen with the glucose and therefore diminishes the oxygen available for quenching fluorescence. The rate of oxidation is proportional to the concentration of glucose. Therefore, the output of the device 36b will be greater than that of the device 36a and the difference is measured by the output of the device. The system includes a filter 37, OED devices 38 and a processor 39.

Referring now to FIG. 11, the output of each O-ED in FIG. 10 is plotted as a function of time following addition of a blood sample to the DFAD, presuming that the oxygen level of the blood is higher than that of ambient air. In the case of the oxygen sensor 36a the excess oxygen is lost by diffusion to the air and ultimately the output (dotted) curve reaches a steady value of fluorescence that reflects equilibration with air.

However, the modified fiber 36b consumes the oxygen more rapidly due to its reaction with the glucose in the sample, causing a greater rise in fluorescence. When all the glucose that is present in the blood has been consumed, this fiber also equilibrates with ambient air. Thus, the two curves ultimately merge. FIG. 12 is a curve representing the integration of the space between the two curves and therefore its area is a measure of the total amount of glucose in the sample.

Referring now to FIG. 13, a plot is shown in the case of continuous monitoring where the dual FAD device is implanted within a patient. (See also FIGS. 22 and 23 below and the description thereof). The first portion of the curve represents normal variations in glucose level in the blood and the large increase represents a large increase in glucose level after, for example, a patient has had a meal. The solid curve represents the output of device 36b and the broken line curve represents the output of device 36a. FIG. 14 is a plot of the difference between the curves of FIG. 13, therefore of the variation with time of the glucose level of the patient.

Referring now to FIG. 15, a single FAD of a multiple FAD system is shown as an example of an immunoassay described in FIG. 9 above. The FAD comprises an innermost sheath 41 whose index of refraction $n_s$ is greater than the index of refraction $n_c$ of the core and which contains an antigen-fluorescein complex designated as A* in quantity sufficient to fully saturate an antibody located in sheath 43. Sheath 42 is a sheath which is hydrophilic and contains reflective particles and which is impermeable to antigen (A) when dry but permeable when wet. Sheath 43 is hydrophilic and contains as a reagent, an antibody Ab to the antigens A* and A. (A is the analyte of interest.) The outermost sheath 44 is microporous. A sample of fluid containing the antigen A is added to sheath 44.

The kinetics of diffusion and reaction of the system are as follows:

A diffuses through sheath 44 into sheath 43 and A* diffuses through sheath 42 into sheath 43. The following competing reversible reactions occur in sheath 43.

  (1)

  (2)

The antibody complexes A*—Ab and A—Ab cannot diffuse out of sheath 43. There is enough A* in sheath 41 to saturate the Ab in sheath 43. Assuming the case of no antigen A in the sample, reaction (1) will proceed to a state of equilibrium at which time the rate of diffusion of A* out of sheath 41 will equal the rate of diffusion of A* back into sheath 41. At that time the output will become constant, as shown by the lower curve in FIG. 16. Virtually all of A* is bound to Ab, yielding a low level of fluorescence. The middle curve represents the case when the sample contains a finite quantity of A; and the upper curve represents the case where A>>A* so that very little Ab—A* is formed.

The spacing of the curves in FIG. 16 is arbitrary. It will be apparent that in actuality this spacing will depend upon the concentration of A* in sheath 41 and the concentration of A in the sample. By employing a bundle of FADs each containing a different concentration of A* in sheath 41, one of the devices will contain an optimum concentration of A* such that the spacing of the curves is optimum. By means of the logic selector 45, the output of that device will be selected and the others rejected. By calibration the concentration of A in the sample may be determined.

Yet another method for utilizing the specificity and high sensitivity of immunoassays is shown by FIGS. 17 and 18. FIG. 17 illustrates in detail a single element of an array of several FADs, each containing different concentrations of antibody Ab. The core c is permeable to the product Y of a reaction

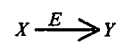

wherein E is an enzyme, X is high molecular weight and Y is low molecular weight. Sheath 50 is permeable to Y but not to X; sheath 51 contains an antibody Ab and an antigen-enzyme complex A—E wherein the enzyme E is active. This complex reacts with antibody in accordance with the following reversible reaction.

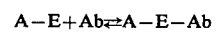

Enzyme E is inactive in A—E—Ab. Sheath 50 has a lower index of refraction than the index of refraction of core c, in order to reflect all the light along the axial path within the core.

This system is intended to measure analyte A, which is an antigen, in a fluid sample. Sheath 51 is microporous and permeable to A. When sheath 51 is wetted with a sample containing the antigen A, it diffuses into sheath 51 but no further. There it reacts with Ab, displacing A—E in direct proportion to their relative concentrations. The A—E that is released catalyzes the reaction, forming Y which then diffuses into the core where it is detected by light that is transmitted along the core. If the wavelength of light is selected for maximum absorbance by Y and sheath 51 contains an excess of X the method will be highly sensitive and specific for the presence of A in the sample fluid. FIG. 18 describes the electrical output of the system following the application of the sample to sheath 51. As in FIG. 9 this analytical method will require the use of a switching system so as to measure the curve for the element that contains the optimum quantity of Ab—A—E. The rate of change of output from that element will then be proportional to the concentration of A in the sample.

Referring now to FIG. 19, an FAD is shown comprising a core c and a sheath 52 having a lower refractive index than the core or containing reflective material (or surrounded by a reflective sheath, not shown). The sheath 52 is permeable to analyte (i.e. an antigen, A) but not to higher molecular weight components of the sample. The core contains antibody Ab bonded to a dye D to form the complex Ab—D. Light at the absorption peak of the dye is transmitted through core c. The dye exhibits the property that its absorptive powers are changed when the antigen binds to Ab—D. When sample is applied to sheath 55, antigen A (the analyte of interest) diffuses through this sheath and into core c, which is selected for this purpose. The reversible reaction

occurs.

This causes a shift in the amount of light transmitted through the element. By using a set of elements with varying concentrations of Ab—D one may select the optimum element for the level of A in the fluid. Since the reaction of A with Ab—D is reversible this may be used for continuous monitoring.

When measuring the analyte concentration in a discrete fluid sample, it is necessary to apply a reproducible volume of fluid uniformly to the analytical element described herein. While this can be achieved by a skilled operator utilizing micro pipettes, it is intended here to describe another means whereby this may be achieved in a simpler fashion. It will be seen that this is a unique feature of the elements described herein.

Referring now to FIG. 20, a means for uniformly saturating an FAD is shown which employs the phenomonen of wicking. The FAD shown consists of a core c and a single sheath S. The same means may be employed with FADs containing several sheaths and two or more FADs.

A base 60 is shown comprising a rigid support 61. Adhered to the top of the base is a hydrophilic coating 62 which is wetted with the sample which is used in excess to that needed to wet the FAD. The sample fluid will diffuse through the base to the FAD. It will ascend by capillary action to the top of the FAD. Provided the height of the device is not excessive, the wicking or capillary effect will result in a uniform wetting of the sheath S.

The analytical device described herein may be adapted to permit the measurement of large molecular weight analytes that do not normally permeate sheaths in a selective fashion. FIG. 21 describes such a device that is useful for determining the quantity of enzyme in a fluid sample. The core c is permeable to a dye D and is transmissive to light with a wavelength selected for maximum absorption by D. The dye D is chemically bound to a hydrophilic polymer that is incorporated into sheath 57. Sheath 58 is permeable to D, impermeable to higher molecular weight components of the fluid, and selected from materials with a lower refractive index than the core. The chemical bond between the dye and the polymer will be selected so it can be selectively degraded by the enzyme in the fluid that one wishes to detect. Thus, for example, if one wishes to measure the concentration of esterase in plasma, utilize an ester linkage between the dye and the polymer. This can be accomplished e.g. by use of any of the dyes classed as acidic dyes, reacted with the hydroxyl groups in gelatin.

When the element is wet by a sample, D will be enzymatically released and diffuse into the core where it will be detected by a decrease in light transmission through the element. The rate of change in light transmission will be proportional to the concentration of the enzyme.

One of the advantages of the fiber embodiment of the invention is that it can be readily incorporated in a catheter for insertion into the body, for example, into a vein or an artery. A suitable form of catheter-fiber structure is shown in FIG. 22.

Referring to FIG. 22, a catheter 70 is formed in two parts, namely a tip portion 71 and a body portion 72. These are made of suitable material such as polypropylene, polyethylene, silicone rubber, polyvinyl chloride, or poly (ethylene vinylacetate) and may have a diameter of, for example, 0.5 to 1.5 mm, appropriate for a particular purpose such as, for example, insertion into a vein or an artery. A cylindrical fiber-shaped device 73 is affixed, for example in a spiral configuration as shown, to the tip 71 such that it is exposed to the body fluid when the catheter is implanted. The fiber 73 has protruding tips 73a and 73b. The exposed fiber 73 (either all or a portion of it) is susceptible to penetration by an analyte and is of a construction such as that shown in any of FIGS. 2, 3, 7, 9, 10 or 19, hereinabove. The body 72 of the catheter is formed with parallel passages 75 into which fiber extensions 73a and 73b are inserted, these being recessed so as to form sockets 77. The fiber extensions 73a and 73b may be bare optical fiber or they may be coated with a protective coating. When the tip 71 and the body portion 72 are assembled in operative condition the protruding tips 73a and 73b will be received in the sockets 77 and will be in physical and optical contact with the fiber extensions 75a, thereby providing a continuous optical path from a source of exciting radiation to the output end.

With such a catheter continuous monitoring of a body fluid is possible with an appropriate readout to inform the diagnostician, either visually or by printout or by both means.

Referring now to FIG. 23, another form of catheter is shown which comprises a housing 80 through which an optical fiber 81 passes and which also supports an extension 82 of the optical fiber having a portion 82a exposed to body fluids. The exposed portion 82a may be constructed as in any of FIGS. 2, 3, 7, 9, 10 or 19 above. The projections 81a of fibers 81 and 82, project into sockets 83 in a tip 84 which embodies a prism 85. When the tip 84 and the housing 80 are brought together a continuous light path is provided through the optical fiber 81 the prism and the optical fiber 81a.

GENERAL DISCUSSION

It will be apparent that the invention may be manifested in numerous forms and is capable of numerous applications. Structurally there are at least two elements one of which, exemplified by the transmissive core is a medium for transmitting energy in continuous form such as electro-magnetic energy, e.g. ultraviolet light or visible light, electric current (AD or DC) or sonic energy. The other element (or elements) is a sheath or sheaths. The configuration is preferably rod-like with a transmissive core in the form of a fiber typically about 10 $\mu$m to 1 mm in diameter with one or more sheaths surrounding the core typically about 10 $\mu$M to 100 $\mu$M in thickness. The active length of the device (i.e., the length which is wetted by the test fluid) may vary from about 0.5 cm or less to 1 meter or more. In most bioassay applications the length will not exceed about 10 cm. Departures from such dimensions are permissible. As stated above, other configurations, e.g. polygonal configurations, are permissible.

The core, besides its transmissivity and shape, may have the following characteristics: It may be impermeable to aqueous liquids. If permeable it may contain a reagent, e.g. a dye, or it may be devoid of a dye and be a receptor for permeation by a reagent. Suitable materials for impermeable cores are quartz, polymethylmethacrylate, polycarbonate, polystyrene, etc. If the core is permeable, suitable materials are plasticized polyvinyl chloride, polyurethanes, polypropylene, nylon, gelatin, polyvinyl alcohol, natural rubber, butyl rubber, cis-polyisoprene, poly (ethylene vinyl acetate). The index of refraction of the core, $n_c$, may be greater or less than that of the adjacent sheath.

The material and construction of the sheaths will depend upon their function. In all cases when a reaction occurs in a sheath or where a liquid must diffuse into, through or out of a sheath, it should be permeable to water. Permeable sheaths may be permeable to large and small molecules and to finely divided solids suspended in a liquid sample, or they may be selective with regard to permeability such that unwanted large molecules, etc. are excluded, as taught in the book by Crank and Park, "Diffusion in Polymers." One or more sheaths may contain a reagent or a precursor of a reagent and such reagent or precursor may be immobile or mobile and it may undergo a reaction such as enzymatic cleavage to render its product mobile or it may undergo a reaction such as antibody-antigen reaction which makes it immobile. All such physical states of sheath material and reagents are possible and methods of synthesis or forming are well known to those practiced in the art.

Elements of the dimensions suitable for this invention e.g. (1–100 μm diameter) can be made by normal fiber-forming techniques; the Encyclopedia of Polymer Science and Technology provides an adequate description of these techniques. Briefly, there are three major techniques: melt forming, wet forming, and dry forming. Melt forming is used for thermoplastic polymers (e.g. polypropylene) that exhibit a low viscosity when heated above their melting point. Wet process forming consists of extruding a solution of the polymer in a solvent and passing the fiber through a bath of a second solvent. This bath solvent has the property that it will dissolve the polymer solvent, but not the polymer; thus the solvent is extracted by the bath solvent, leaving a pure polymer fiber. Dry forming consists of extruding a solution of polymer and volatile solvent into a heated air stream, where the solvent evaporates.

Adaptations of these processes can be used to coat the core fiber with the sheaths. If the central fiber is made from a high melting point material (e.g. glass), one could coat it with a melted polymer. It is more likely that one will use polymer solutions, especially when it is necessary to incorporate chemicals that are used to react with analyte or otherwise participate in the required chemical analysis. Many such reagents degrade under conditions of high temperature.

If, for example, one wanted to form an assymmetric microporous membrane as the outer sheath as is required for the enzyme assay described above (FIG. 21), one could use wet forming. The polymer and dye-polymer conjugate would be dissolved in a solvent and coated onto the fiber by pulling the fiber (c, coated with sheath 58) through an orifice that has the solution on the upstream side. On the downstream side is a bath with a solvent that is selected to elute the primary solvent leaving a polymer sheath 57 that has microscopic holes. The bath solvent is selected so as to be a non-solvent for both the polymer and the dye-polymer conjugate.

Once formed as a continuous, long coated fiber, it will be cut into short lengths and mounted in a holder, whose purpose is to align the ends of the fiber into a reproducible position, to provide a simple means to insert the fiber into the instrument (cf. FIG. 1), and a means to protect the fiber during storage and use. The housing could also be within a catheter for use as a monitoring instrument as shown in FIGS. 22 and 23. The catheter could be inserted into the fluid or body cavity of interest; it contains highly conductive input and output fibers that are coupled to each end of the coated fiber assay system so as to introduce exciting radiation and to recover the analyte-modified radiation. These housings will generally be made of plastic material and are understood to be fabricated by the standard methods available, namely, injection molding, transfer molding, extrusion, epoxy molding, or heat forming.

Reagents, reagent pre-cursors, reflective material, etc. which may be incorporated in various sheaths include the following: enzymes, $O_2$-quenchable fluorescent molecules (e.g. fluoranthrene), antibodies, dyes, fluorescent dyes, reflective materials ($TiO_2$, $SiO_2$, etc.), dye-polymer products. These and other reagents, reagent pre-cursors and reflective materials are well known to those skilled in the art.

It will therefore be apparent that new and useful apparatus and methods are provided for chemical and biochemical analyses.

I claim:

1. A method for the quantitative analysis of oxygen in a fluid, said method comprising:
   (a) providing a fiber-sheath element including a fiber capable of transmitting electromagnetic energy in the visible and ultraviolet ranges and defining a path for the transmission of said energy, a first oxygen-permeable sheath surrounding said fiber, an oxygen-quenchable dye incorporated into the material forming said fiber or said sheath and means for reflecting said electromagnetic radiation from said sheath into said fiber;
   (b) introducing ultraviolet light into one end of said fiber whereby a portion of said ultraviolet light reacts with said fluorescent dye to produce fluorescence and emission of visible light, said emission of visible light being cumulative along a length of said path; and
   (c) contacting said fiber-sheath element with said fluid whereby oxygen permeates said element and quenches said fluorescence by reaction with said dye to reduce the visible light emitted from said fiber-sheath element in proportion to the amount of oxygen contained in said fluid.

2. The method of claim 1 wherein a multiplicity of said fiber-sheath elements are employed, said elements containing said oxygen-quenchable fluorescent dye in different concentrations.

3. The method of claim 1 wherein said fluorescent dye is fluoranthrene.

4. The method of claim 1 wherein said fluorescent dye is contained in said sheath.

5. The method of claim 1 wherein said fluid is a liquid.

6. The method of claim 5 wherein said liquid is blood.

7. A method for the quantitative analysis of an analyte in a fluid containing said analyte species and a second species which reacts with said analyte species in the presence of a catalyst, said method comprising:
   (a) providing a fiber-sheath element including:
      a fiber which transmits electromagnetic radiation;
      a first sheath element covering said fiber and formed of a material which is permeable to at least one of said analyte species and said second species and which contains a reagent which reacts with one of said analyte species and said second species to modify an electromagnetic energy transmitting characteristic of the fiber; and
      a second sheath element surrounding said first sheath element, said second sheath element being formed of a material which is permeable to both said analyte species and said second species and which contains a catalyst for causing a reaction between said analyte species and said second species;

(b) contacting said element with the fluid to be analyzed thus allowing said analyte and said second species to permeate said second sheath element and to react in the presence of said catalyst, thereby diminishing the amount of the species reacting with said reagent;

(c) transmitting electromagnetic radiation through said fiber with cumulative modification of said radiation along a length of said fiber due to the influence of said reagent; and (d) measuring the quantity of electromagnetic radiation of at least one wavelength emitted from said fiber.

8. The method of claim 7 further comprising:
providing an additional fiber-sheath element without said catalyst in said second sheath, and
correlating the difference between the amount of said electromagnetic radiation emitted by the two fibers to the amount of analyte present in the fluid.

9. The method of claim 8 wherein ultraviolet light is introduced from the same light source into one end of each of said fibers and wherein said reagent is a fluorescent material and the emitted electromagnetic radiation which is measured is light in the visible range.

10. The method of claim 9 wherein said analyte is glucose, said second species is oxygen, said catalyst is glucose oxidase and said reagent is an oxygen-quenchable fluorescent dye.

11. A method, in accordance with claim 1 or 7, wherein the fluid is a liquid and wherein one end only of said fiber-sheath element is contacted with a mass of hydrophilic material containing said liquid to be analyzed in an amount in excess of that necessary to wet said element whereby capillary action carries said liquid through the sheath to uniformly wet said element.

12. A method for quantitative analysis of an antigen A1 contained in a liquid, said method comprising:
(a) providing a fiber element capable of transmitting electromagnetic energy and defining a path for the transmission of said energy, a first sheath surrounding said fiber element and containing a first complex A2 of an antigen and an energy-modifying compound, a second sheath surrounding said first sheath, said second sheath reflecting said electromagnetic radiation and being selectively permeable to said first complex when wet, and a third sheath, surrounding said second sheath, and an antibody Ab to A1 and A2 incorporated into the material forming said third sheath;

(b) contacting said fiber element with said liquid whereby said sheaths are wetted and antigen A1, if present, diffuses from the liquid into said third sheath to complex said antibody and said first complex diffuses reversibly across said second sheath into said third sheath and likewise complexes with said antibody to produce the following competing reversible reactions in said third sheath:

$$A1 + Ab \rightleftharpoons A1 \cdot Ab \quad (1)$$

$$A2 + Ab \rightleftharpoons A2 \cdot Ab \quad (2)$$

(c) introducing the electromagnetic radiation into one end of said fiber whereby a portion refracts into said first sheath wherein said refracted portion reacts with said energy-modifying compound to produce a modification of the transmitted radiation which is cumulative along a length of said path and which is proportional to the amount of A1 diffusing into said fiber element.

13. The method of claim 12 wherein a multiplicity of said fiber elements are employed, said fiber elements containing said complex A2 of an antigen and an energy-modifying compound in different concentrations.

14. The method of claim 12 wherein said energy-modifying compound is a fluorescent compound, wherein said electromagnetic radiation introduced into the fiber is ultraviolet light, and said modification is conversion to visible light by fluorescence.

15. A method for the quantitative analysis of an antigen A1 contained in a liquid, said method comprising:
(a) providing a fiber-sheath element including a fiber which transmits electromagnetic radiation, said fiber having an index of refraction $n_c$ and being permeable to the product Y of a reaction:

$$X \xrightarrow{E} Y$$

wherein E is an enzyme, X is a high molecular weight compound and Y is a low molecular weight compound; a first sheath surrounding said fiber and being permeable to Y but not to X; a second sheath surrounding said first sheath and having an index of refraction $n_s$ lower than $n_c$, said second sheath being formed of a material containing an antibody Ab immunobonded to a complex of an enzyme E and an antigen A2, and an excess of X, said second sheath being permeable to A1;

(b) transmitting electromagnetic radiation selected for maximum modification by Y through said fiber;

(c) wetting said second sheath with the liquid to be analyzed, whereby any antigen A1 present in the liquid diffuses into second sheath and reacts with Ab thereby displacing A2—E in proportion to the concentration of A1 in the liquid, the displaced complex A2—E catalyzing the conversion of X into Y which then diffuses into the fiber and modifies said electromagnetic radiation cumulatively along a length of said fiber.

16. The method of claim 15 wherein a plurality of said fiber-sheath elements are provided, said elements containing different amounts of X.

17. A method for the quantitative analysis of an antigen contained in a liquid, said method comprising:
(a) providing a fiber-sheath element including a fiber which transmits electromagnetic radiation and which is formed of a material containing an antibody Ab, for the antigen, bonded to a compound Y in the form of a complex Ab-Y, said compound Y having an energy-modifying characteristic which changes upon immunobonding of the antigen to the antibody Ab; and a sheath, permeable to the antigen, surrounding said fiber;

(b) transmitting electromagnetic radiation selected for maximum modification by Y through said fiber;

(c) wetting said sheath with the liquid to be analyzed, whereby any antigen present in the liquid diffuses through the sheath and into the fiber to immunobond with Ab thus modifying said characteristic of Y and said electromagnetic radiation cumulatively, along a length of said fiber.

18. A method for the quantitative analysis of an enzyme in a liquid sample, said method comprising:
(a) providing a fiber-sheath element including a fiber which transmits electromagnetic radiation, a sheath surrounding said fiber and formed of a hydrophilic polymer and an energy modifying compound Y incorporated into and chemically bound to said polymer, said chemical bond being selectively degradable by the enzyme to be detected, said fiber being permeable to Y;

(b) transmitting electromagnetic radiation selected for maximum modification by Y through said fiber; and (c) wetting said sheath with the liquid to be analyzed whereby any enzyme in the liquid breaks down the chemical bond between Y and the polymer, thus releasing Y for diffusion into the fiber wherein Y modifies said radiation, cumulatively, along a length of said fiber.

19. A process in accordance with claim 15, 17 or 18 wherein Y is a dye which produces said modification of said transmitted energy by absorption.

20. The method of claim 17 or 18 wherein a plurality of said fiber-sheath elements are provided, said elements containing different amounts of Y.

21. A method, in accordance with claim 12, 15, 17 or 18 wherein one end only of said fiber-sheath element is contacted with a mass of a hydrophilic material containing the liquid to be analyzed in an amount in excess of that necessary to wet said element whereby capillary action carries said liquid through said coating to uniformly wet said fiber-sheath element.

22. A method for the quantitative analysis of an analyte contained in a fluid, said method comprising:

(a) providing a plurality of fiber-sheath elements, each of said elements including: (1) an electromagnetic energy transmissive fiber defining a path for transmission of electromagnetic energy, at least a portion of said fiber being formed of a material having an electromagnetic energy transmitting characteristic capable of modification by the presence of an analyte contained in the fluid; (2) a semipermeable sheath surrounding said fiber; and (3) a reagent which modifies said transmitted energy responsive to the presence of an analyte or which reacts with the analyte to form a product which modifies said transmitted energy, said elements containing said reagent in different amounts;

(b) contacting said fiber-sheath elements with the fluid to be analyzed;

(c) transmitting electromagnetic radiation through said fibers with cumulative modification of said radiation along a length of each of said fibers due to the influence of said reagent; and (d) taking the output of one of said fibers as a measurement of the concentration of the analyte and rejecting the output of the other fibers.

* * * * *